(12) United States Patent
Bisping

(10) Patent No.: US 6,430,425 B1
(45) Date of Patent: Aug. 6, 2002

(54) ELECTRODE ARRANGEMENT FOR MEDICAL CATHETERS

(76) Inventor: Hans Jurgen Bisping, An Lutterbuschgen 12, 52072 Aachen (DE)

( * ) Notice: Subject to any disclaimer, the term of this patent is extended or adjusted under 35 U.S.C. 154(b) by 33 days.

(21) Appl. No.: 09/638,931

(22) Filed: Aug. 15, 2000

(30) Foreign Application Priority Data

Aug. 16, 1999 (DE) .......................... 199 38 775
Nov. 2, 1999 (DE) .......................... 199 52 679

(51) Int. Cl.⁷ .................... A61B 5/042; A61B 18/14; A61N 1/05
(52) U.S. Cl. ................... 600/374; 606/41; 607/122
(58) Field of Search ................ 600/374, 380, 600/381; 606/41, 49; 607/119, 122, 124

(56) References Cited

U.S. PATENT DOCUMENTS

| 4,532,924 A | * | 8/1985 | Auth et al. ............. 606/50 |
| 5,545,161 A | * | 8/1996 | Imran .................... 606/41 |
| 5,643,255 A | | 7/1997 | Organ .................... 606/41 |
| 5,676,662 A | * | 10/1997 | Fleischacker et al. ..... 606/41 |
| 6,033,403 A | * | 3/2000 | Tu et al. ................ 606/41 |

* cited by examiner

*Primary Examiner*—Lee Cohen
(74) *Attorney, Agent, or Firm*—Charles L. Schwab; Nexsen Pruet Jacobs & Pollard, LLC

(57) ABSTRACT

A catheter electrode shell (2) has cutouts (3) made in such a way that a closed circular ring (4) is preserved to secure the electrode shell (2) to the catheter tube. The remaining contact surface (5) is arranged on the outside of the catheter curvature in the case of pre-bent or guided catheters.

10 Claims, 6 Drawing Sheets

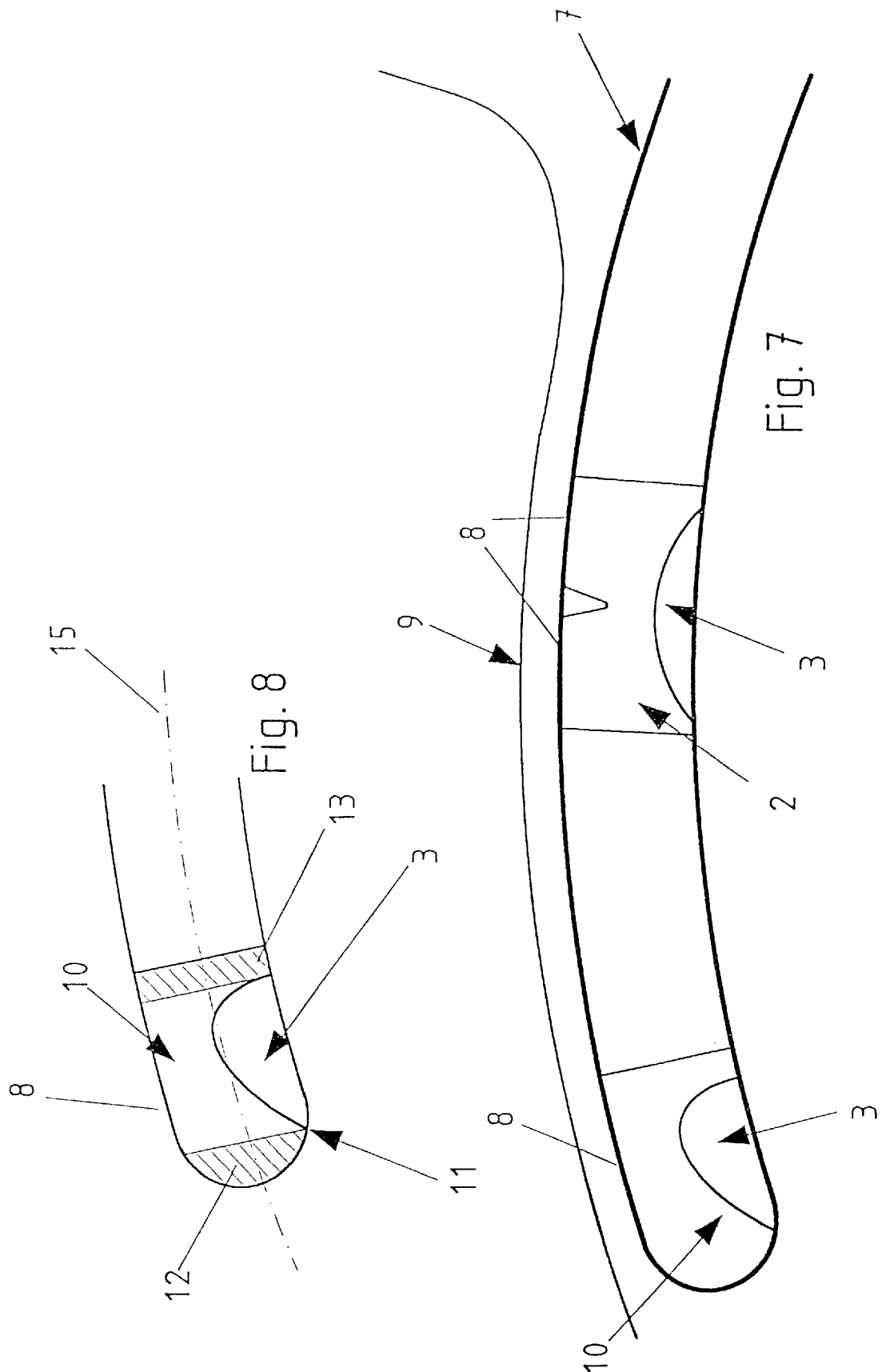

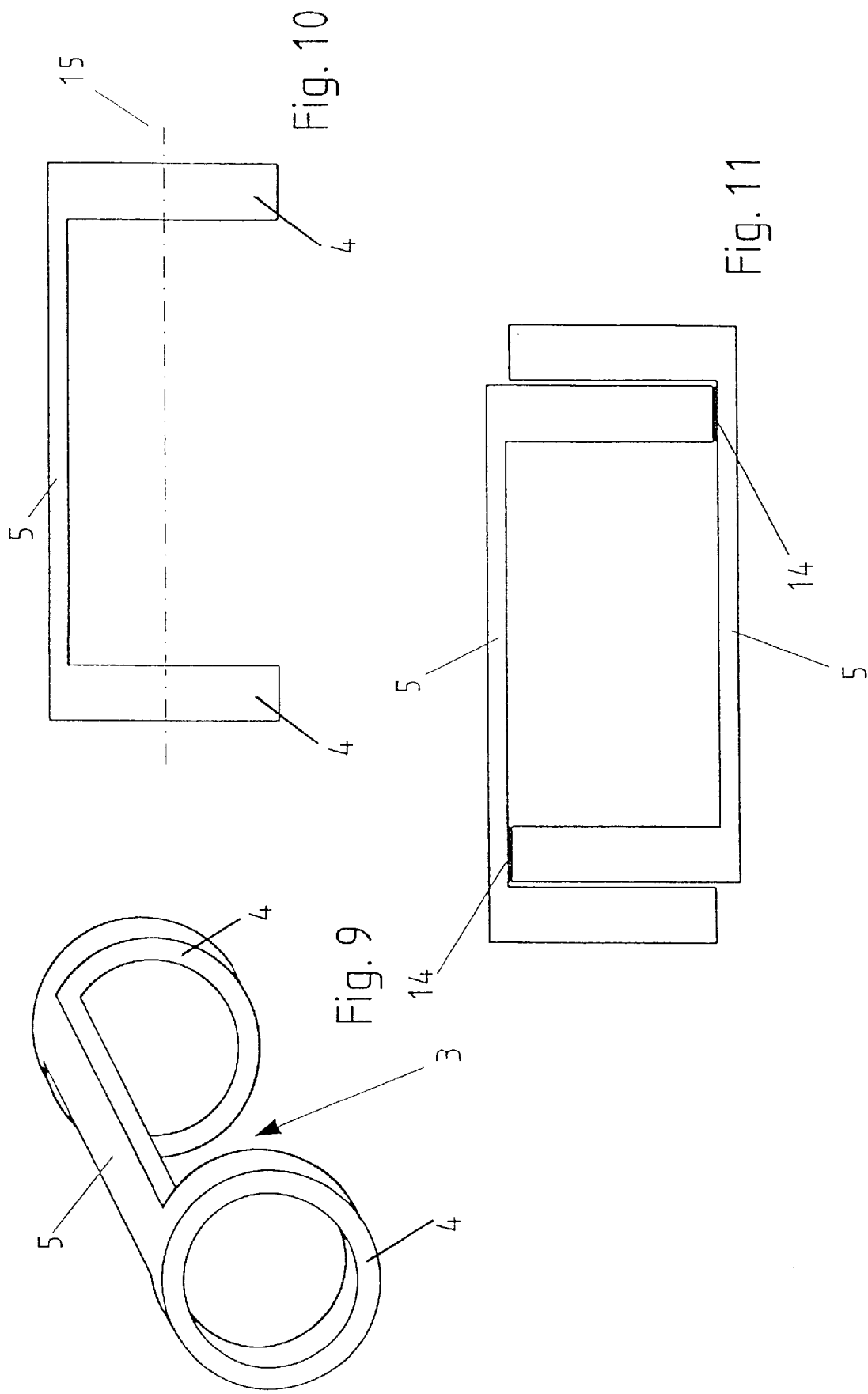

ELECTRODE ARRANGEMENT FOR MEDICAL CATHETERS

TECHNICAL FIELD

This invention relates to temporary and permanent medical catheters such as are used, for example, in heart pacemaker and defibrillator therapy as well as in electrophysiological research.

BACKGROUND ART

Medical catheters are used either as diagnostic catheters with pure detection function or as therapeutic catheters with detection, stimulation and ablation function with high frequency energy, hereinafter referred to as HF energy. It is conceivable that the present invention can be used with both non-guided and guided catheters. The construction of such prior art catheters has, in principle, been the same for decades, and include:

Shell-shaped electrodes made of stainless steel or Pt/Ir are drawn over a plastic hose with cavities which is made of, for example, PVC, nylon, polyurethane or similar material, and connected to wires located in the interior of the catheter for the conveyance of electrical energy.

A typical electrode size is, for example, 6F (1F roughly corresponds to 0.33 mm) with a shell or electrode length of 2 to 10 mm. While diagnostic usually have a certain specified curvature at their distal ends guided catheters in the rest state are initially straight and can be brought to a desired curvature from the distal end by the operator, such curvature sometimes far exceeding a 90° angle with a radius of curvature of 2 to 4 cm.

The objective of this pre-curvature or pre-bending is to achieve a certain wall contact in the heart or in another body part, depending on the application, in order to improve the extracted signal strength or, when the electrode is a stimulation or ablation electrode, to guarantee optimal energy transfer by good wall contact with the tissue. In ablation with HF energy, in particular, the geometrical dimensions of the electrode shells, or of the so-called electrode head, also called electrode tip, takes on special importance. In what follows, the electrode configuration according to the invention is explained for the example of an ablation catheter; however, the invention is suitable for other applications.

In usage, an ablation catheter is pressed against the tissue at a certain location in the body by appropriate manipulation, by stiffness of the catheter itself, by an appropriately selected pre-curvature or, in the case of guided catheters, by a curvature that is operator controlled.

If body tissue is also yielding, only a certain part of the electrode shell or of the electrode tip comes in intimate contact with the tissue, while the other part of the electrode comes to lie more-or-less without wall contact and is then inevitably bathed by tissue fluid—thus by blood, in the case of ablation catheters for cardiological application. Because blood exhibits a lower resistance than tissue, the energy delivered is distributed according to the resistance ratios. This leads to the surrounding blood being undesirably heated instead of the HF energy being directed to the tissue in order to produce the appropriate desired lesions there.

An electrode configuration addressing this problem is disclosed in U.S. Pat. 5,643,255 for a Steerable Catheter with Rotatable Tip Electrode and Method of Use issued on Jul. 1, 1997 to Leslie W. Organ. In this prior United States patent, a tip electrode is provided on a catheter which is insulated on one side and rotatably supported so that the electrode position can be adjusted from outside in such a way that the uninsulated surface comes in contact with the tissue to be ablated and thus the desired ablation result is brought about. To insulate parts of an electrode surface, however, requires a relatively expensive manufacturing process.

So-called split electrodes are also known, which have an electrode shell split in two on the longitudinal axis or which have an electrode head split into four parts.

The individual electrode elements in the above-cited cases must be electrically insulated relative to one another. In these prior catheter concepts, the mechanical arrangement of the electrode shells on the plastic hose is difficult to accomplish.

OBJECTS AND DISCLOSURE OF THE INVENTION

It is an object of the invention to create an electrode configuration that, on the one hand, guarantees favorable electrical properties and, on the other hand, is easy to manufacture and guarantees reliable mechanical functioning.

While, in the previously known electrode shells, the entire surface is in operative connection with the media surrounding it, it is proposed according to the invention that the electrode shell or the electrode tip has cutouts of predetermined size and shape. These cutouts can be in the form of a single hole or multiple holes, slots, perforations, or milled grooves of predetermined curved shape. It is important, however, that an electrode shell whose surface has been reduced in this way can be attached to the plastic hose in the proven manner. According to the invention, this is guaranteed by virtue of the fact that the cutouts are arranged such that at least one electrode shell ring, enclosing the catheter hose in circular fashion is present.

The electrode tip attached to the distal end of the catheter includes an electrode shell with its distal end closed by a cap to form an electrode point.

The cutout according to the invention is arranged such that the electrode tip shell has at least one closed electrode ring required for strength; the electrode ring being arranged, for example, at the proximal end of the tip shell. In order, however, to guarantee that the electrode tip still has a firm grip on the plastic hose at its distal end, the cutout should, according to the invention, be arranged such that the electrode cap extends circumferentially around the end of the catheter hose, so that a further closed distal "ring" is created.

The electrode configurations brought about by the before mentioned cutouts have reduced areas. These remaining residual areas should preferably face toward the tissue being treated. It is therefore proposed that these residual areas be arranged essentially on the outside of the catheter curvature in the case of pre-bent or externally bendable catheters.

According to a preferred embodiment of the invention, sensors for energy control are placed in the plastic hose and/or beneath the electrode shell at the transitions from the cutouts to the electrode surfaces. These are preferably temperature probes for the control of the catheter temperature in HF energy ablation.

In further development of the invention it is proposed that instead of a circular configuration of the catheter hose, as well as the electrode shell and the electrode tip, it is made elliptical, at least in portions. This variant has the advantage that the overall catheter arrangement has a flexurally soft direction of curvature and a flexurally stiff direction of curvature. As is well known, an elliptical section hose bends easier in one direction than in a direction at right angles to the one direction. For the user, this concept has the advantage that the user can exert greater pressing forces in the flexurally stiff direction. In line with this, it is further proposed that the residual surfaces of the electrode shell left over by a corresponding cutout are arranged on one of the elliptical catheter sides with the tighter radius of curvature.

The electrode shell is easier to manufacture if the cutout is made such that only a closed circular ring and a contact surface with a free end is the resulting configuration. Two or more such electrode shells are then arranged on a catheter hose in such a way that the free end of one such electrode shell comes to lie beneath the closed circular ring of the neighboring electrode shell.

It is proposed that several electrode-shell configurations are also interlocked or chained in such a way that they form, for example, tripolar or quadripolar configurations.

In further development of the invention it is proposed that the entire external or internal surface of the closed circuit ring be provided with an insulating layer. The insulating layer applied to the inside of the ring then serves for electrical insulation relative to the contact surface of a neighboring electrode shell; the externally arranged insulation prevents the surface of the closed circular ring being added to the total contact surface.

Further advantages of the invention can be inferred from the description of the drawing, in which the exemplary embodiments of the invention are described in more detail.

BRIEF DESCRIPTION OF THE DRAWINGS

FIG. 7 is a side view of a distal catheter end with electrode tip and electrode shell according to the invention.

FIG. 8 is a side view of an electrode tip.

FIG. 9 is a perspective view of an electrode shell with a large cutout.

FIG. 10 is a side view of the shell shown in to FIG. 9.

FIG. 11 is a side view of two interlocked shells of the type shown in FIG. 9.

BEST MODE FOR CARRYING OUT THE INVENTION

Figure 1:
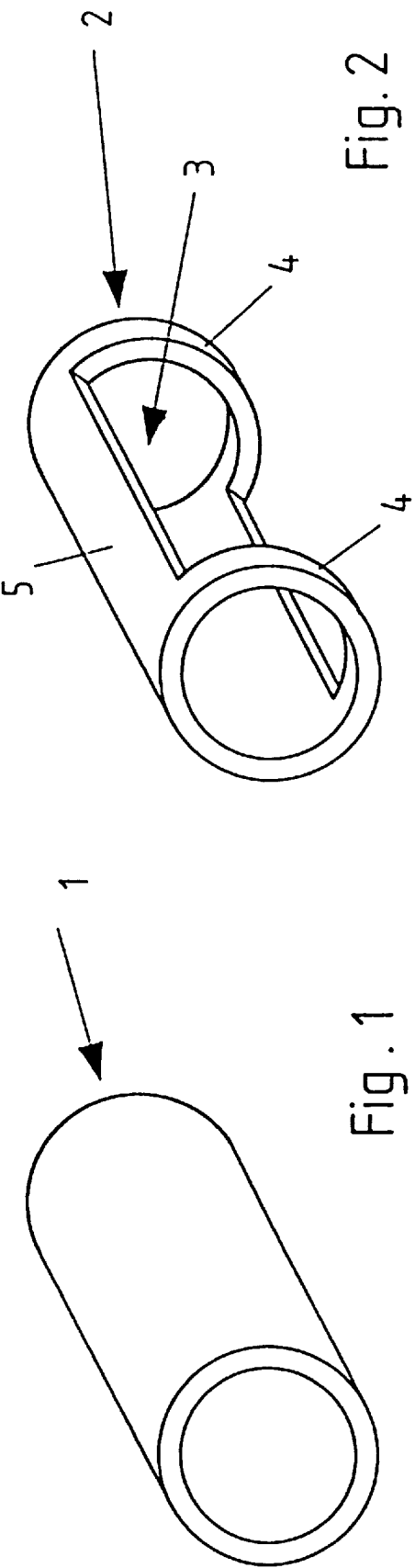
FIG. 1 is a perspective view of a conventional electrode shell.

FIG. 1 shows a conventional shell 1 of an electrode with closed cylindrical surface. Its mechanical grip on the catheter hose is effected by cementing or by shrinking processes or by swelling processes.

Figure 2:
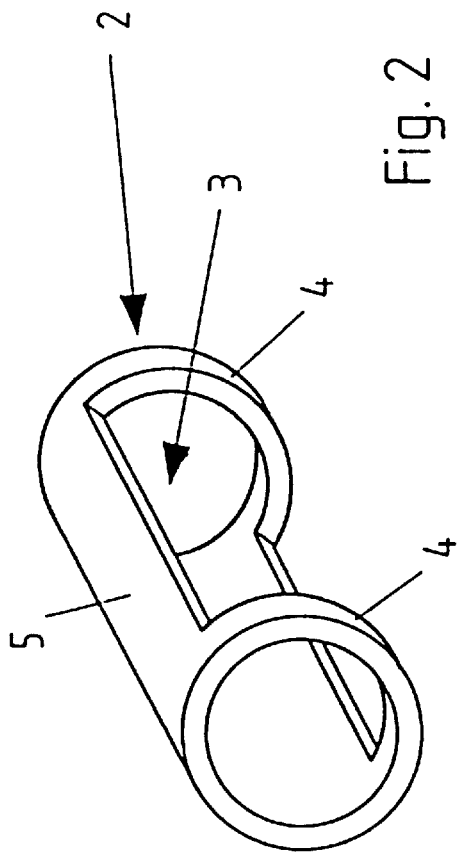
FIG. 2 is a perspective view of an electrode shell with a cutout.

In the exemplary embodiment of FIG. 2, an electrode shell 2 with a rectangular cutout 3 is shown. An electrical contact surface 5 is formed essentially by the residual surface, the remaining circular rings 4 guaranteeing good mechanical fixation on the catheter hose. If such an electrode shell 2 with cutout 3 comes to lie in a curve of a catheter 7, the cutout 3 also has a positive effect in that it enhances the flexibility and bendability of the whole catheter 7 at the curve, because the catheter hose material can "bulge out" in this region of cutout 3 upon curving.

Figure 3:
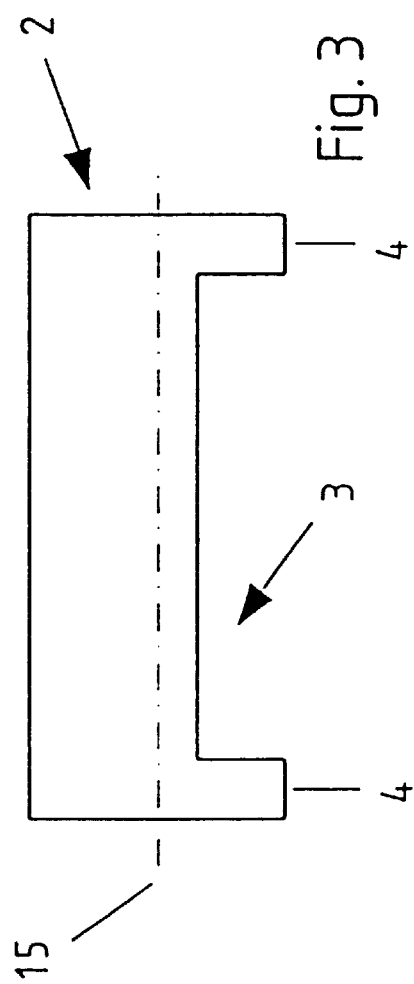
FIG. 3 is a side view of the shell shown in FIG. 2.
Figure 4:
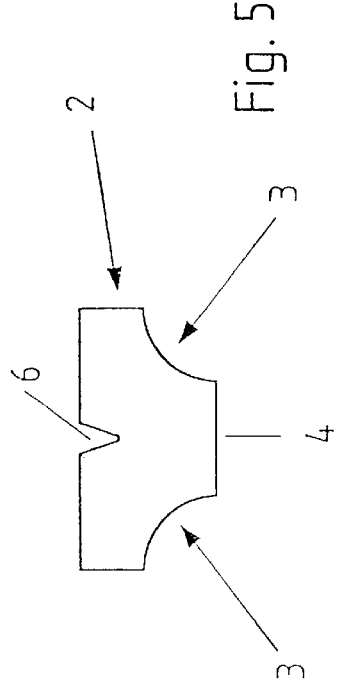
FIG. 4 is a side view of a shell with an elliptical cutout.
Figure 5:
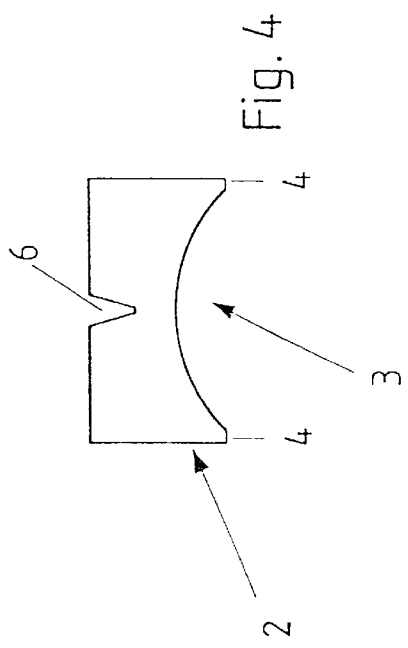
FIG. 5 is a side view of a shell with two arc-shaped cutouts.

FIG. 3 shows the side view of the electrode shell 2 of FIG. 2, the remaining circular rings 4 guaranteeing mechanical stability. Without these circular rings 4 encircling the catheter hose, the reduced contact surface 5 could be fastened to the catheter hose only by very great effort. FIGS. 4 and 5 show variations of cutouts 3. An elliptical cutout 3, arranged such that closed circular rings 4 are left at both ends of electrode shell 2, is seen in FIG. 4. Reference numeral 6 identifies a notch or a slot, which serves to enhance the flexibility upon curving of the catheter 7. Several such slots in the remaining electrode surface could be provided to enhance flexibility. In the exemplary embodiment of FIG. 5, cutouts 3 are arranged at both ends of the electrode shell 2 in such a way that the closed circular ring 4, necessary for mechanical strength, is arranged roughly in the middle of electrode shell 2.

Figure 6:
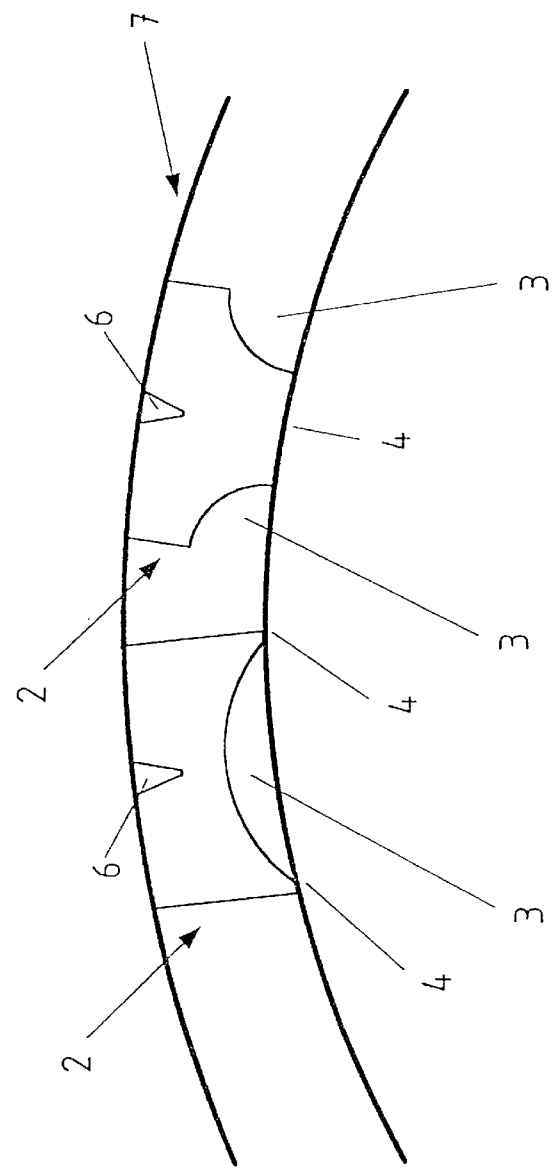
FIG. 6 is a side view of a catheter part with two electrode shells according to the invention arranged thereon.

FIG. 6 shows a part of a catheter 7 with curvature, to which two electrode shells 2 of the type shown in FIGS. 4 and 5 are affixed. It should be noted that in both cases the cutouts 3 are located on the inside of the radius of curvature and, accordingly, the largest electrically effective surface of electrode shells 2 lies on the radially outer side of the curved catheter 7.

FIG. 7 shows how the catheter 7, with an electrode tip 10 and an electrode shell 2 some distance from the electrode tip 10, is supported with its external surface against a tissue wall 9. The electrode tip 10 and the electrode shell 2 are arranged in such a way that their largest surface region 8 lies on the outside of the catheter curvatures and accordingly they make effective electrical contact with tissue wall 9.

FIG. 8 shows another development of the electrode point or the electrode tip 10. Cutout 3 in this embodiment is arranged so that a circular ring 13, indicated by shading, remains at the proximal end of the electrode tip. Its existence guarantees that the electrode tip 10 has a firm grip on the catheter hose. The distal section line 11 of cutout 3 with electrode cap 12 according to FIG. 8 is chosen such that electrode cap 12 is still large enough to form another closed ring, indicated by shading, which is necessary for mechanical strength. This is always the case when the electrode cap 12 extends past the end of the catheter hose.

If the cutout 3 were enlarged in the direction toward the distal end of catheter 7, the section line 11 would move farther toward central axis 15 of the catheter until, finally, the closed "ring equivalent" is no longer formed. The mechanical fixation of the entire electrode 10 would then become questionable.

FIGS. 9 to 11 show a further variation of the cutout 3. This is an extremely large cutout 3, which on the one hand still leaves two closed circular rings 4 but on the other hand leaves a very narrow contact surface 5. It is proposed that the area removed by cutout 3 is at least 70% of the total external area of the uncut electrode shell 2, so that the remaining contact surface 5 is at most 30% of the original uncut shell.

If two of the cut-out electrode shells shown in FIG. 5 are interlocked as shown in FIG. 11 and electrical contact between the two electrode shells is blocked by insulating layers 14, then two electrically separate contact surfaces 5 lie opposite one another, and an orthogonal electrode system is formed, which has well-known advantages in signal extraction. An advantage of this arrangement is that it is relatively easy to manufacture and simultaneously has high mechanical strength. Other electrode-shell configurations according to the invention may also be interlocked in this way.

Figure 13:
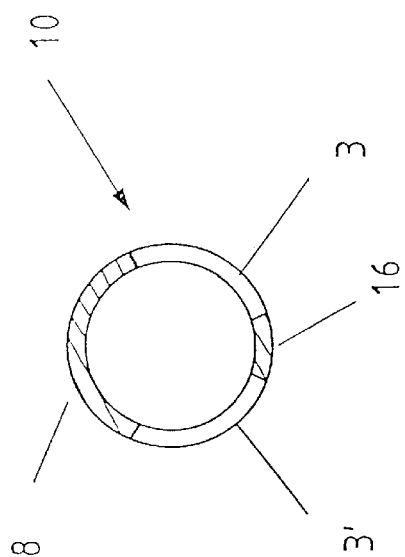
FIG. 13 is a section of taken on the line A-B in FIG. 12.
Figure 12:
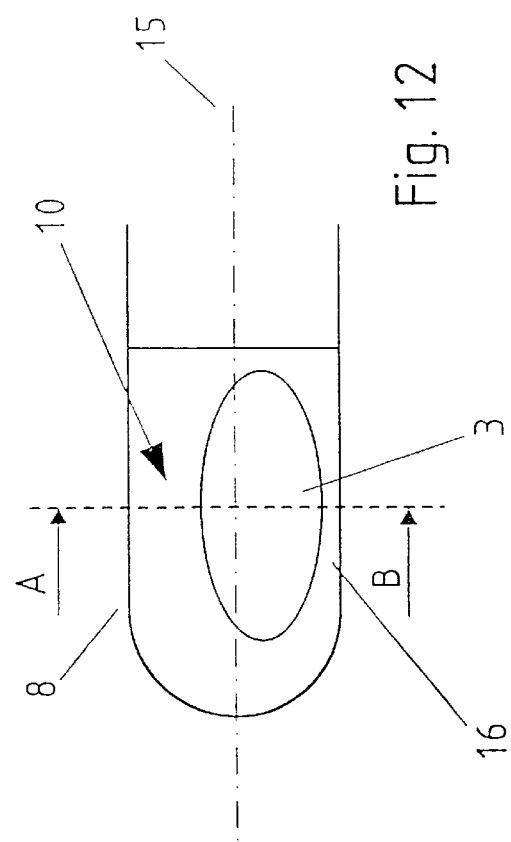
FIG. 12 shows the side view of an electrode tip with laterally applied elliptical cutouts.

The exemplary embodiment of FIG. 12 has a further variation of cutout 3. Here two substantially laterally arranged cutouts 3, 3' are arranged on electrode tip 10. Although only one can be seen in FIG. 12, the other one lies symmetrically with respect to it on the other side. In this illustrated modification, the closed ring 13 shown in FIG. 8, is present on the proximal part. In addition, a closed web 16 remains on the underside of the electrode tip shown in FIG. 12, which web again guarantees the desired mechanical stability. FIG. 13 is a section of the before-cited arrangement along section line A–B.

Figure 14:
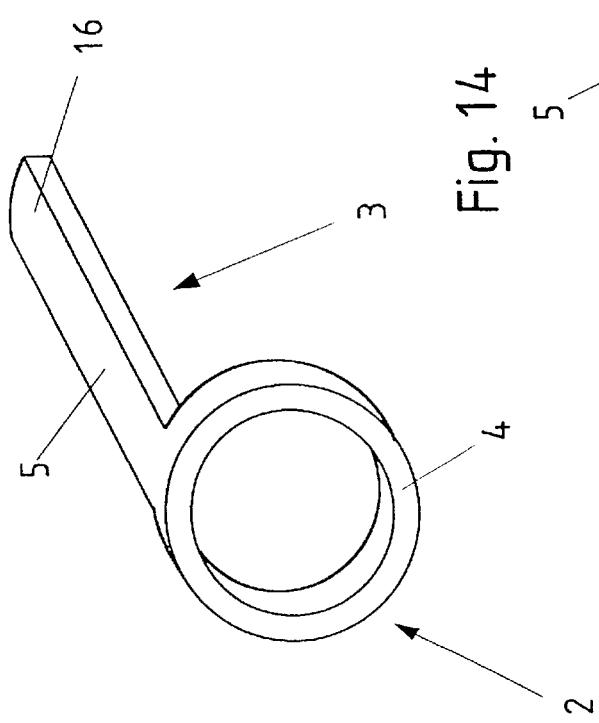
FIG. 14 is a perspective view of an electrode shell with a contact surface with a free end and a circular ring.

In the exemplary embodiment of FIG. 14, an electrode shell 2 with rectangular cutout 3 is shown. Electrical contact surface 5 is substantially formed by the residual surface. One end of contact surface 5 makes a transition to a circular ring 4, which guarantees good mechanical fixation on the catheter hose. The second end of contact surface 5 terminates in a free end 16.

Figure 15:
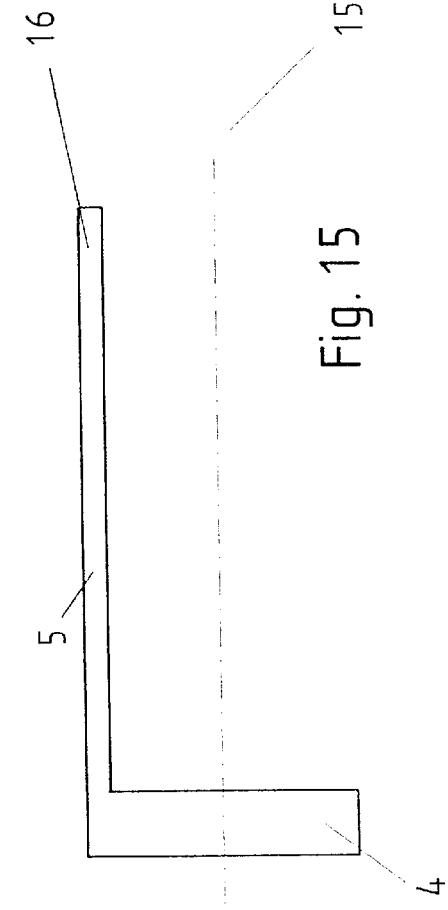
FIG. 15 is a side view of the electrode shell shown in FIG. 14.

FIG. 15 shows the side view of the electrode shell of FIG. 14.

Figure 16:
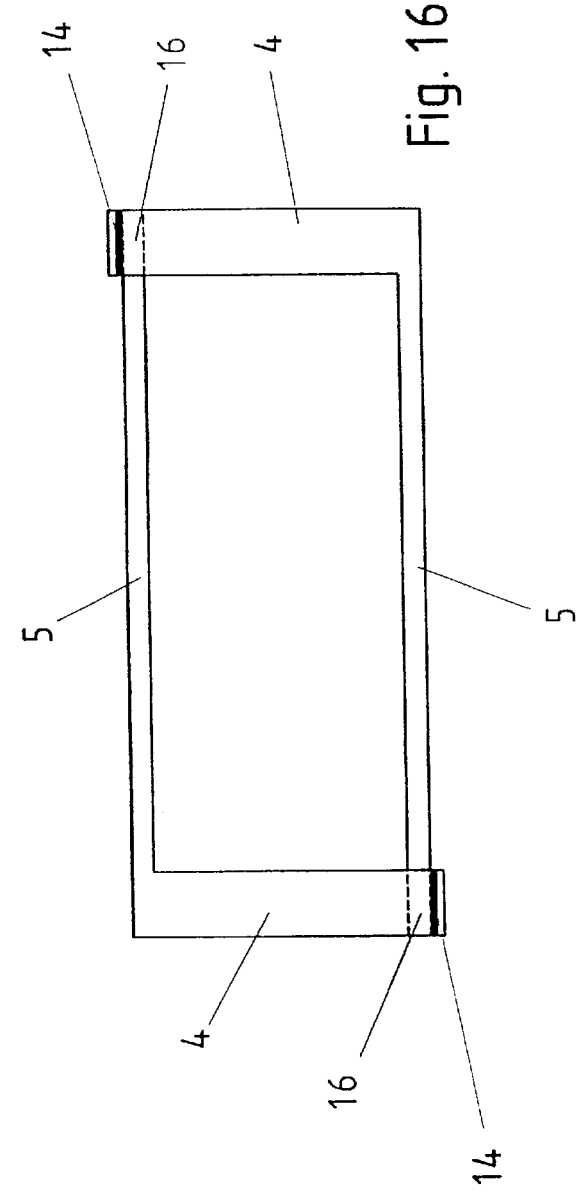
FIG. 16 is s side view of two interlocked electrode shells of the type shown in FIG. 14.

If two electrode shells 2 of the type shown in FIG. 14 are interlocked as shown in FIG. 16 and electrical contact between the two electrode shells 2 is blocked by insulating layers 14; then two electrically separate contact surfaces 5 lie opposite one another and an orthogonal electrode system exists, which has well-known advantages in signal extraction. The advantage of this arrangement is that it is easy to manufacture and nevertheless has high mechanical strength.

What is claimed is:

1. A medical catheter (7) of the type having a catheter hose, comprising: a pair of electrode shells (2), each having cutouts (3) producing a closed circular ring (4) and a contact surface (5) extending from said closed circular ring (4) with a free end (16), said electrode shells (2) being arranged on said catheter hose in intertwined relation to one another with their free ends (16) positioned beneath each others circular ring (4).

2. The medical catheter (7) of claim 1 and further comprising a layer of electrical insulation on the insides of said circular rings (4).

3. A medical catheter (7) of the type having a hose with a distal end, and further comprising:
   a cylindrical electrode secured to the exterior of said hose near its distal end including an electrode shell (2) having
      a pair of spaced rings (4) at the opposite ends of said shell (2) and
      an elliptical cutout (3) in one side of said electrode and between said rings (4).

4. The medical catheter (7) of claim 3 and further comprising a slot (6) in said electrode shell (2) intermediate its opposite ends and in diametrical opposed relation to said cutout (3).

5. The medical catheter (7) of claim 4 wherein said hose has a radius of curvature and said cutout (3) is on the inside of said curvature.

6. The medical catheter (7) of claim 3 wherein said medical catheter (7) is elliptical in cross section.

7. A medical catheter (7) of the type having a catheter hose, comprising:
   two cylindrical electrode shells (2), each having a cutout (3), rings (4) at opposite sides of said cutout (3) and an external contact surface (5) extending between said rings (4), said electrode shells (2) being positioned on said catheter hose to place said external contact surface (5) of one of said electrode shells (2) on the diametrically opposite side of said catheter hose from said external contact surface (5) of the other of said electrode shells (2) and placing said rings (3) of one of said shells (2) in juxtaposed relation to the rings (3) of the other of said shells (2) and
   electrical insulation elements (14) between said two electrode shells (2), said insulation elements (14) preventing electrical contact of said two electrode shells (2).

8. A medical catheter (7) of the type having a catheter hose having a distal end, comprising,
   an electrode tip (10) having a proximal end and
   a distal end closed by a cap (12) which includes a portion forming a ring encompassing the distal end of said hose
   at least one oval cutout (3) between said cap (12) and said proximal end leaving a closed ring (13) on said proximal end of said tip (10).

9. The medical catheter of claim 8 wherein said tip (10) has two circumferentially spaced oval cutouts (13) between said cap (12) and said proximal end of said tip (10).

10. A medical catheter (7) of the type having a catheter hose comprising:
   a cylindrical electrode secured to the exterior of said hose including an electrode shell (2) having
      axially opposite ends and diametrically opposite sides,
      a cutout (3) in each of said ends at one of said diametrically opposite sides of said shell (2) and
      a slot (6) in the other of said diametrically opposite sides of shell (2) intermediate said axially opposite ends.

* * * * *